(12) United States Patent
Li et al.

(10) Patent No.: US 9,453,935 B2
(45) Date of Patent: Sep. 27, 2016

(54) GANTRY CONFIGURATION FOR COMBINED MOBILE RADIATION INSPECTION SYSTEM

(71) Applicants: Nuctech Company Limited, Haidian District, Beijing (CN); Tsinghua University, Haidian District, Beijing (CN)

(72) Inventors: Jianmin Li, Beijing (CN); Yuanjing Li, Beijing (CN); Chunguang Zong, Beijing (CN); Quanwei Song, Beijing (CN); Tao Xue, Beijing (CN); Qingjun Zhang, Beijing (CN); Sheng Tang, Beijing (CN)

(73) Assignees: Nuctech Company Limited, Haidian District, Beijing (CN); Tsinghua University, Haidian District, Beijing (CN)

( * ) Notice: Subject to any disclaimer, the term of this patent is extended or adjusted under 35 U.S.C. 154(b) by 0 days.

(21) Appl. No.: 14/412,512

(22) PCT Filed: Jul. 2, 2013

(86) PCT No.: PCT/CN2013/078655
§ 371 (c)(1),
(2) Date: Jan. 2, 2015

(87) PCT Pub. No.: WO2014/005508
PCT Pub. Date: Jan. 9, 2014

(65) Prior Publication Data
US 2015/0192689 A1    Jul. 9, 2015

(30) Foreign Application Priority Data

Jul. 4, 2012  (CN) .......................... 2012 1 0230078

(51) Int. Cl.
G01V 5/00    (2006.01)
G01N 23/04   (2006.01)
F16M 11/42   (2006.01)

(52) U.S. Cl.
CPC .......... *G01V 5/0016* (2013.01); *F16M 11/425* (2013.01); *G01N 23/04* (2013.01)

(58) Field of Classification Search
CPC ............ G01V 5/0008; G01V 5/0016; G01V 5/0066; F16M 11/425
USPC ........................................... 250/393
See application file for complete search history.

(56) References Cited

U.S. PATENT DOCUMENTS 4,760,260 A * 7/1988 Walsh .................... G01T 1/163
250/363.02
5,077,479 A * 12/1991 de la Barre ............. G21K 1/02
250/363.1

(Continued)

FOREIGN PATENT DOCUMENTS

CN    1133440 A    10/1996
CN    2383069 Y    6/2000

(Continued)

OTHER PUBLICATIONS

International Search Report for corresponding International Patent Application No. PCT/CN2013/078655 mailed Oct. 24, 2013.

(Continued)

*Primary Examiner* — Marcus Taningco
(74) *Attorney, Agent, or Firm* — Merchant & Gould P.C.

(57) ABSTRACT

The present invention discloses a gantry configuration for a combined mobile radiation inspection system comprising a first arm frame, a second arm frame and a third arm frame. The first, second and third arm frames define a scanning channel to allow an inspected object to pass therethrough. The gantry configuration for the combined mobile radiation inspection system further comprises a position sensing device configured to detect a position error between the first arm frame and the second arm frame; and a controller configured to control a moving speed of at least one of the first arm frame and the second arm frame based on the detected position error, so that the position error between the first arm frame and the second arm frame is equal to zero. Compared with the prior art, the present invention is advantageous at least in that an automatic deviation correction device is provided on the gantry arm frame, and thus the position error between both side arm frames can be automatically controlled to zero, so that the gantry arm frame can be effectively prevented from being subjected to a force and deforming, and the radiation detector can receive the full ray, thereby improving the imaging quality.

11 Claims, 3 Drawing Sheets

(56) References Cited

U.S. PATENT DOCUMENTS

| | | | |
|---|---|---|---|
| 5,692,028 A | 11/1997 | Geus et al. | |
| 5,838,759 A * | 11/1998 | Armistead | 378/57 |
| 6,563,903 B2 | 5/2003 | Kang et al. | |
| 6,937,692 B2 * | 8/2005 | Johnson et al. | 378/57 |
| 7,453,987 B1 | 11/2008 | Richardson | |
| 7,497,618 B2 | 3/2009 | Chen et al. | |
| 7,519,147 B1 | 4/2009 | Aloisio | |
| 7,663,109 B2 | 2/2010 | Kang et al. | |
| 2004/0125914 A1 | 7/2004 | Kang et al. | |
| 2004/0179647 A1 | 9/2004 | Zhao et al. | |
| 2004/0247075 A1 | 12/2004 | Johnson et al. | |
| 2004/0258198 A1 * | 12/2004 | Carver et al. | 378/57 |
| 2007/0269007 A1 | 11/2007 | Akery | |
| 2008/0023631 A1 * | 1/2008 | Majors et al. | 250/336.1 |

FOREIGN PATENT DOCUMENTS

| | | |
|---|---|---|
| CN | 2567568 Y | 8/2003 |
| CN | 101417773 A | 4/2009 |
| CN | 201864484 U | 6/2011 |
| CN | 202757895 U | 2/2013 |
| JP | 2006-518463 A | 8/2006 |
| JP | 2006-527368 A | 11/2006 |
| NZ | 330920 A | 10/1999 |
| RU | 2 251 683 C2 | 5/2005 |
| RU | 2 378 641 C2 | 1/2010 |
| RU | 2 381 490 C2 | 2/2010 |
| WO | 2008/133765 A2 | 11/2008 |

OTHER PUBLICATIONS

Chinese Office Action for corresponding Chinese Patent Application No. 201210230078.3 mailed Mar. 27, 2015, 8 pgs.

Extended European Search Report for corresponding European Patent Application No. 138133152 mailed Feb. 2, 2016, 8 pgs.

Japanese Office Action for corresponding Japanese Patent Application No. 2015-518819 mailed Jan. 18, 2016, 4 pgs.

Russian Decision to Grant for corresponding Russian Patent Application No. 2015103210 mailed Feb. 9, 2016, 16 pgs, with English translation.

Wu, J., "Analysis of positioning and correcting method of Gantry crane in shipyard", Mechanical and Electrical Information Journal, (2012), 12: 57-58. English Abstract.

Japanese Office Action for corresponding Japanese Patent Application No. 2015-518819 mailed Jul. 11, 2016.

* cited by examiner

GANTRY CONFIGURATION FOR COMBINED MOBILE RADIATION INSPECTION SYSTEM

This application is a National Stage Application of PCT/CN2013/078655, filed Jul. 2, 2013, which claims the benefit of Chinese Patent Application No. 201210230078.3 filed on Jul. 4, 2012 in the State Intellectual Property Office of China, and which applications are incorporated herein by reference. To the extent appropriate, a claim of priority is made to each of the above disclosed applications.

BACKGROUND OF THE INVENTION

1. Field of the Invention

The present invention relates to a technical field of radiation inspection, more particularly, relates to a gantry configuration for a combined mobile radiation inspection system.

2. Description of the Related Art

In prior art, a gantry combined mobile radiation inspection system is a large container/vehicle radiation inspection system, and a core technology of which is a radiation imaging technology. The gantry combined mobile container/vehicle radiation inspection system is a container/vehicle safety inspection system used in seaport, border, airport, etc., and has a special modular design in structure, therefore, it can be simply assembled and disassembled, without a need to construct a fixed protection construction, and without a need to construct a radiation protection wall. An imaging device of the gantry combined mobile container/vehicle radiation inspection system is a gantry arm frame. The container/vehicle to be inspected is located below the gantry arm frame and in the middle of fixed rails. The gantry arm frame moves on the fixed rails. A ray emitted from a radiation source provided on one side arm frame passes through the inspected container/vehicle and is received and processed by a radiation detector provided on the other side arm frame, so as to form a scan image.

The gantry arm frame moves on the fixed rails and is constrained by the fixed rails, and basically it cannot derail from the fixed rails. Accordingly, in the prior art, a synchronization problem about moving speeds of both side arm frames generally is not considered.

However, in a practical inspection process, it still requires the moving speeds of both side arm frames to conform to each other when the gantry arm frame moves on the fixed rails. If the moving speeds of both side arm frames are different, the gantry arm frame is subjected to a force and deforms. Although the deformation of the gantry arm frame may be very small, it still produces a big influence on the accurate radiation detection system. Once the gantry arm frame deforms, the radiation detector cannot receive the full ray, and thus the imaging quality will be deteriorated. Thereby, it is necessary to control a position error between the both side arm frames by means of an automatic deviation correction system during movement of the gantry arm frame on the fixed rails, so as to obtain an accurate scan image.

In the prior art, the deviation correction of the gantry arm frame is mainly achieved by a manual operation, and there is not a deviation correction means and a synchronous control means. Because of an actual mechanical manufacturing error, a motor rotation speed error, etc., the effect of the manual deviation correction is not ideal. So, it is necessary to improve the deviation correction of the gantry arm frame in the prior art.

SUMMARY OF THE INVENTION

The present invention has been made to overcome or alleviate at least one aspect of the above mentioned disadvantages.

According to an aspect of the present invention, there is provided a gantry configuration for a combined mobile radiation inspection system, comprising: a first arm frame configured to be movable along a first rail; a second arm frame, opposite to the first arm frame, configured to be movable along a second rail parallel to the first rail; and a third arm frame connecting the first and second arm frames, so as to move with the first and second arm frames. The first, second and third arm frames together define a scanning channel to allow an inspected object to pass therethrough. The gantry configuration for the combined mobile radiation inspection system further comprises a position sensing device configured to detect a position error between the first arm frame and the second arm frame, and a controller configured to control a moving speed of at least one of the first arm frame and the second arm frame based on the detected position error, so that the position error between the first arm frame and the second arm frame is equal to zero.

According to a preferable embodiment of the present invention, a laser pointer is provided on one of the first arm frame and the second arm frame, and a position sensitive device is provided on the other of the first arm frame and the second arm frame. The position sensitive device is configured to detect an actual position of a laser beam, which is emitted from the laser pointer, illuminated on the position sensitive device. The position error between the first arm frame and the second arm frame is determined according to a difference between the actual position and a predetermined target position. When the laser beam emitted from the laser pointer is illuminated at the predetermined target position on the position sensitive device, the position error between the first arm frame and the second arm frame is determined to be equal to zero.

According to another preferable embodiment of the present invention, a radiation source is mounted on one of the first arm frame and the second arm frame and configured to emit a ray onto the inspected object passing through the scanning channel, and a radiation detector is mounted on the other of the first arm frame and the second arm frame and configured to receive the ray emitted from the radiation source.

According to another preferable embodiment of the present invention, the controller is provided on the first arm frame or the second arm frame.

According to another preferable embodiment of the present invention, the controller calculates a target rotation speed of an electric motor, for driving the first or second arm frame to move, based on the position error detected by the sensing device, and the controller controls the electric motor to rotate with the calculated target rotation speed, so as to control the position error between the first arm frame and the second arm frame to become zero.

According to another preferable embodiment of the present invention, the controller calculates the target rotation speed of the electric motor based on the position error by means of a PID algorithm.

According to another preferable embodiment of the present invention, a frequency converter, for controlling the rotation speed of the electric motor, is provided on the first arm frame or the second arm frame, and the target rotation speed is used as an instruction value for controlling the electric motor by the frequency converter.

According to another preferable embodiment of the present invention, an encoder, for detecting an actual rotation speed of the electric motor, is provided on the first arm frame or the second arm frame, and the controller controls the rotation speed of the electric motor based on a rotation speed difference between the target rotation speed and the actual rotation speed detected by the encoder, so that the rotation speed of the electric motor is controlled to be equal to the target rotation speed.

According to another preferable embodiment of the present invention, the controller controls the rotation speed of the electric motor based on the rotation speed difference by means of a PID algorithm.

According to another preferable embodiment of the present invention, the controller is configured to be a programmable logic controller.

According to another preferable embodiment of the present invention, the arm frame, on which the radiation detector is provided, contains lead for radiation protection.

According to another preferable embodiment of the present invention, the first, second and third arm frames are detachably assembled together.

According to another preferable embodiment of the present invention, the first and second arm frames extend in a vertical direction and the third arm frame extends in a horizontal direction.

Compared with the prior art, the present invention is advantageous at least in that an automatic deviation correction device is provided on the gantry arm frame, and thus the position error between both side arm frames can be automatically controlled to be equal to zero, so that the gantry arm frame can be effectively prevented from being subjected to a force and deforming, and the radiation detector can receive the full ray, thereby improving the imaging quality.

DETAILED DESCRIPTION OF PREFERRED EMBODIMENTS OF THE INVENTION

Figure 1:
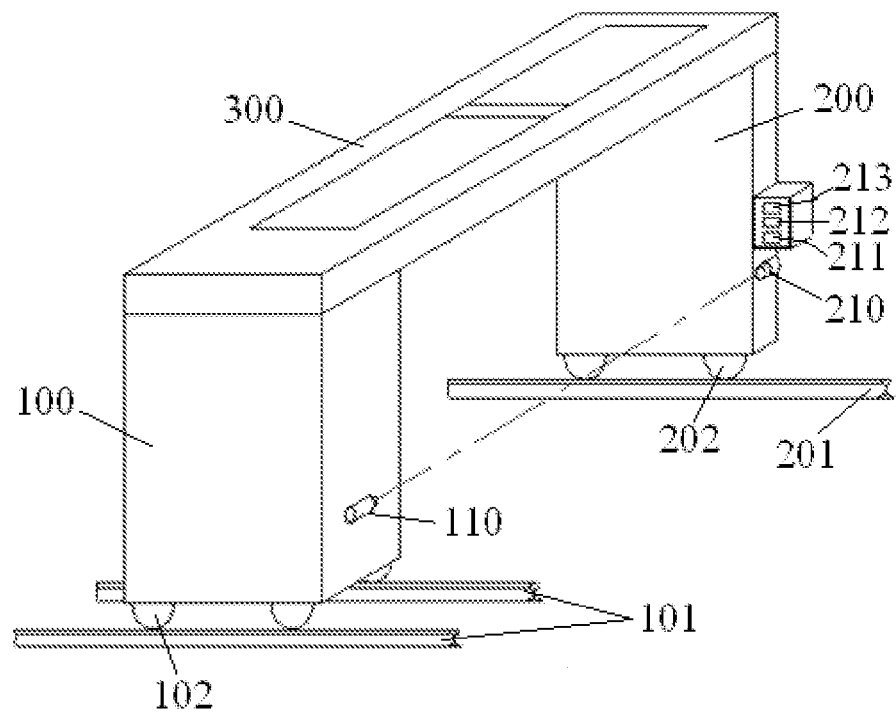
FIG. 1 is an illustrative perspective view of a gantry configuration for a combined mobile radiation inspection system according to an embodiment of the present invention.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

FIG. 1 is an illustrative perspective view of a gantry configuration for a combined mobile radiation inspection system according to an embodiment of the present invention.

As shown in FIG. 1, in an embodiment of the present invention, the gantry configuration for the combined mobile radiation inspection system mainly comprises a first arm frame 100, a second arm frame 200 and a third arm frame 300.

As shown in FIG. 1, the first arm frame 100 moves on a first rail 101 by means of wheels 102 provided on the bottom of the first arm frame 100. The second arm frame 200, opposite to the first arm frame 100, is arranged parallel to and spaced from the first arm frame 100. The second arm frame 200 moves on a second rail 201, parallel to the first rail 101, by means of wheels 202 provided on the bottom of the second arm frame 200. The third arm frame 300 connects the first and second arm frames 100, 200, so as to move with the first and second arm frames 100, 200. In this way, the first, second and third arm frames 100, 200, 300 together define a scanning channel to allow an inspected object to pass therethrough.

In a preferable embodiment of the present invention, the first, second and third arm frames 100, 200, 300 are detachably assembled together. In this way, the entire radiation inspection system can be simply disassembled, assembled and shipped.

In the preferable embodiment shown in FIG. 1, the first and second arm frames 100, 200 are vertical arm frames extending in a vertical direction, and the third arm frame 300 is a horizontal arm frame extending in a horizontal direction. In this way, a rectangular gantry structure is formed.

Although it is not shown, a radiation source is mounted on one of the first arm frame 100 and the second arm frame 200. The radiation source is configured to emit a ray onto the inspected object (not shown) passing through the scanning channel. In addition, a radiation detector is mounted on the other of the first arm frame 100 and the second arm frame 200. The radiation detector is configured to receive the ray emitted from the radiation source.

It should be noted that herein the position error (position deviation) between the first arm frame 100 and the second arm frame 200 in the moving direction thereof (an extending direction of the rails) should be equal to zero, so that the radiation detector can receive the full ray emitted from the radiation source.

However, in the practical application, since the first arm frame 100 and the second arm frame 200 separately move, the moving speeds of the first arm frame 100 and the second arm frame 200 likely become different. In this condition, it will cause a position error or a position deviation between the first arm frame 100 and the second arm frame 200. In order to overcome this problem, it must keep the moving speeds of the first arm frame 100 and the second arm frame 200 synchronous.

Figure 2:
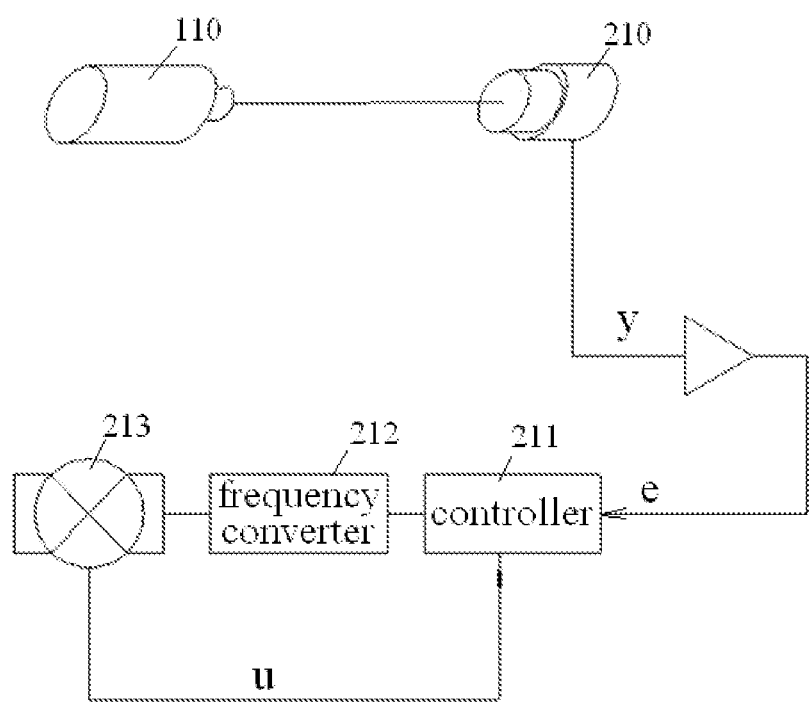
FIG. 2 shows a control process of the gantry configuration for the combined mobile radiation inspection system shown in FIG. 1.

FIG. 2 shows a control process of the gantry configuration for the combined mobile radiation inspection system shown in FIG. 1.

As shown in FIGS. 1-2, in order to keep the moving speeds of the first arm frame 100 and the second arm frame 200 synchronous, the gantry configuration for the combined mobile radiation inspection system according to the present invention further comprises a position sensing device 110, 210 and a controller 211.

As shown in FIGS. 1-2, the position sensing device 110, 210 is configured to detect a position error (position deviation) between the first arm frame 100 and the second arm frame 200. The controller 211 is configured to control the moving speed of at least one of the first arm frame 100 and the second arm frame 200 based on the detected position error e, so that the position error e between the first arm frame 100 and the second arm frame 200 becomes zero.

As shown in FIGS. 1-2, in a preferable embodiment of the present invention, the position sensing device 110, 210 comprises a laser pointer 110 provided on one (e.g., the first arm frame 100) of the first arm frame 100 and the second arm frame 200 and a position sensitive device 210 provided on the other (e.g., the second frame 200) of the first arm frame 100 and the second arm frame 200.

But, in the present invention, the position sensing device is not limited to the illustrated embodiments, for example, the position sensing device may comprise a deformation sensor for detecting the deformation of the horizontal third arm frame 300, and the position deviation between the first arm frame 100 and the second arm frame 200 can be obtained based on the deformation detected by the deformation sensor.

In the illustrated embodiment, the laser pointer 110 is provided on the first arm frame 100, and the position sensitive device 210 is provided on the second arm frame 200.

Figure 3:
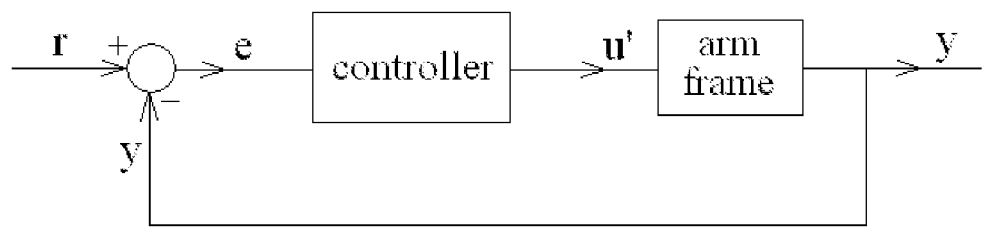
FIG. 3 shows a control frame view to control a position error between a first arm frame and a second arm frame in the gantry configuration for the combined mobile radiation inspection system shown in FIG. 1.

FIG. 3 shows a control frame view to control a position error between a first arm frame and a second arm frame in the gantry configuration for the combined mobile radiation inspection system shown in FIG. 1.

As shown in FIGS. 1-3, the laser pointer 110 is configured to emit a laser beam toward the position sensitive device 210, and the position sensitive device 210 is configured to detect an actual position y of the laser beam, which is emitted from the laser pointer 110, illuminated on the position sensitive device 210. As a result, the position error e between the first arm frame 100 and the second arm frame 200 is determined according to a difference between the actual position y and a predetermined target position r.

It should be noted that, in the present invention, when the laser beam emitted from the laser pointer 110 is illuminated at the predetermined target position (for example, a center position) r on the position sensitive device 210, the position error e between the first arm frame 100 and the second arm frame 200 is determined to be equal to zero. That is, in this condition, the radiation detector receives the full ray emitted from the radiation source.

In an embodiment of the present invention, the controller 211 may be provided on one of the first arm frame 100 and the second arm frame 200. In the embodiment shown in FIG. 1, the controller 211 is provided on the second arm frame 200.

In an embodiment of the present invention, the controller 211 calculates a target rotation speed u' of an electric motor, for driving the first or second arm frame 100 or 200 to move, based on the position error e detected by the sensing device 110, 210. Then, the controller 211 controls the electric motor to rotate with the calculated target rotation speed u', so as to control the position error e between the first arm frame 100 and the second arm frame 200 to become zero.

In the illustrated embodiment, the controller 211 calculates a target rotation speed u' of an electric motor, for driving the second arm frame 200 to move, based on the position error e detected by the sensing device 110, 210. Then, the controller 211 controls the electric motor to rotate with the calculated target rotation speed u', so as to control the position error e between the first arm frame 100 and the second arm frame 200 to become zero. That is, in this embodiment of the present invention, the position error between the first and second arm frames 100, 200 is adjusted to be equal to zero by controlling the moving speed of one of the first and second arm frames 100, 200. But the present invention is not limited to this, and the position error between the first and second arm frames 100, 200 may be adjusted to be equal to zero by controlling the moving speeds of both the first and second arm frames 100, 200 at the same time.

In a preferable embodiment of the present invention, the controller 211 calculates the target rotation speed u' of the electric motor based on the position error e by means of a PID (Proportion Integration Differentiation) algorithm.

Since the PID algorithm is a typical control algorithm, for the purpose of conciseness, its description in detail is omitted herein.

In an embodiment of the present invention, a frequency converter 212, for controlling the rotation speed of the electric motor, is provided on one of the first arm frame 100 and the second arm frame 200. The target rotation speed u' output from the controller 211 is used as an input instruction value of the frequency converter 212 to control the electric motor.

In the embodiment shown in FIG. 1, the frequency converter 212 is provided on the second arm frame 200 and configured to control the rotation speed of the electric motor for driving the second arm frame 200 to move.

In an embodiment of the present invention, an encoder 213, for detecting an actual rotation speed u of the electric motor, is provided on the first arm frame 100 or the second arm frame 200.

In the embodiment shown in FIGS. 1-2, the encoder 213 is provided on the second arm frame 200 and configured to detecting an actual rotation speed u of the electric motor for driving the second arm frame 200 to move.

Figure 4:
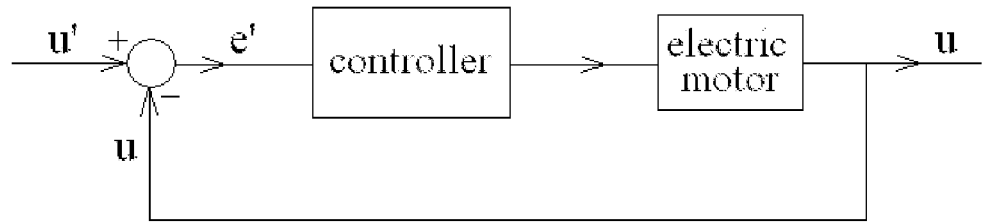
FIG. 4 shows a control frame view to control a rotation speed of an electric motor for driving the second arm frame in the gantry configuration for the combined mobile radiation inspection system shown in FIG. 1.

FIG. 4 shows a control frame view to control a rotation speed of an electric motor for driving the second arm frame in the gantry configuration for the combined mobile radiation inspection system shown in FIG. 1.

As shown in FIGS. 2 and 4, the controller 211 controls the rotation speed of the electric motor based on a rotation speed difference e' between the target rotation speed u' and the actual rotation speed u detected by the encoder 213, so that the rotation speed of the electric motor is controlled to be equal to the target rotation speed u'.

In a preferable embodiment of the present invention, the controller 211 controls the rotation speed of the electric motor based on the rotation speed difference e' by means of a PID algorithm.

In an embodiment of the present invention, the controller may be a programmable logic controller, a single chip microcomputer or a personal computer.

In order to prevent the ray emitted from the radiation source from leakage, as shown in FIG. 1, leak for radiation protection is infused into the first or second arm frame 100 or 200 on which the radiation detector is provided. But the present invention is not limited to this, and the first or second arm frame 100 or 200, on which the radiation detector is provided, may be directly made of radiation protection material.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

What is claimed is:

1. A gantry configuration for a combined mobile radiation inspection system, comprising:
    a first arm frame configured to be movable along a first rail;
    a second arm frame, opposite to the first arm frame, configured to be movable along a second rail parallel to the first rail; and
    a third arm frame connecting the first and second arm frames, so as to move with the first and second arm frames,
    wherein the first, second and third arm frames together define a scanning channel to allow an inspected object to pass therethrough,
    wherein the gantry configuration for the combined mobile radiation inspection system further comprising:
    a position sensing device configured to detect a position error between the first arm frame and the second arm frame; and
    a controller configured to control a moving speed of at least one of the first arm frame and the second arm frame based on the position error detected by the position sensing device, so that the position error between the first arm frame and the second arm frame is equal to zero,
    wherein a radiation source is mounted on one of the first arm frame and the second arm frame and configured to emit a ray onto the inspected object passing through the scanning channel,
    wherein a radiation detector is mounted on the other one of the first arm frame and the second arm frame and configured to receive the ray emitted from the radiation source,
    wherein the arm frame, on which the radiation detector is provided, contains lead for radiation protection.

2. The gantry configuration for the combined mobile radiation inspection system according to claim 1,
    wherein a laser pointer is provided on one of the first arm frame and the second arm frame, and a position sensitive device is provided on the other of the first arm frame and the second arm frame,
    wherein the position sensitive device is configured to detect an actual position of a laser beam, which is emitted from the laser pointer, illuminated on the position sensitive device, and
    wherein the position error between the first arm frame and the second arm frame is determined according to a difference between the actual position and a predetermined target position,
    when the laser beam emitted from the laser pointer is illuminated at the predetermined target position on the position sensitive device, the position error between the first arm frame and the second arm frame is determined to be equal to zero.

3. The gantry configuration for the combined mobile radiation inspection system according to claim 1, wherein the controller is provided on the first arm frame or the second arm frame.

4. The gantry configuration for the combined mobile radiation inspection system according to claim 3,
    wherein the controller calculates a target rotation speed of an electric motor, for driving the first or second arm frame to move, based on the position error detected by the sensing device, and
    wherein the controller controls the electric motor to rotate with the calculated target rotation speed, so as to control the position error between the first arm frame and the second arm frame to become zero.

5. The gantry configuration for the combined mobile radiation inspection system according to claim 4,
    wherein the controller calculates the target rotation speed of the electric motor based on the position error by means of a PID algorithm.

6. The gantry configuration for the combined mobile radiation inspection system according to claim 5,
    wherein a frequency converter, for controlling the rotation speed of the electric motor, is provided on the first arm frame or the second arm frame, and
    wherein the target rotation speed is used as an instruction value of the frequency converter to control the electric motor.

7. The gantry configuration for the combined mobile radiation inspection system according to claim 6,
    wherein an encoder, for detecting an actual rotation speed of the electric motor, is provided on the first arm frame or the second arm frame, and
    wherein the controller controls the rotation speed of the electric motor based on a rotation speed difference between the target rotation speed and the actual rotation speed detected by the encoder, so that the rotation speed of the electric motor is controlled to be equal to the target rotation speed.

8. The gantry configuration for the combined mobile radiation inspection system according to claim 7,
    wherein the controller controls the rotation speed of the electric motor based on the rotation speed difference by means of a PID algorithm.

9. The gantry configuration for the combined mobile radiation inspection system according to claim 1, wherein the controller is configured to be a programmable logic controller.

10. The gantry configuration for the combined mobile radiation inspection system according to claim 1, wherein the first, second and third arm frames are detachably assembled together.

11. The gantry configuration for the combined mobile radiation inspection system according to claim 1, wherein the first and second arm frames extend in a vertical direction and the third arm frame extends in a horizontal direction.

* * * * *